US009621847B2

(12) United States Patent
Mizuhara

(10) Patent No.: US 9,621,847 B2
(45) Date of Patent: Apr. 11, 2017

(54) TERMINAL, SYSTEM, DISPLAY METHOD, AND RECORDING MEDIUM STORING A DISPLAY PROGRAM

(71) Applicant: Takuya Mizuhara, Kanagawa (JP)

(72) Inventor: Takuya Mizuhara, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/995,328

(22) Filed: Jan. 14, 2016

(65) Prior Publication Data

US 2016/0261826 A1 Sep. 8, 2016

(30) Foreign Application Priority Data

Mar. 2, 2015 (JP) .................................. 2015-039781

(51) Int. Cl.
*H04N 7/14* (2006.01)
*A61B 3/113* (2006.01)
(Continued)

(52) U.S. Cl.
CPC ............ *H04N 7/147* (2013.01); *A61B 3/0025* (2013.01); *A61B 3/0041* (2013.01); *A61B 3/113* (2013.01); *A61B 5/0013* (2013.01); *A61B 5/165* (2013.01); *G06F 3/013* (2013.01); *G06K 9/00597* (2013.01); *H04N 7/155* (2013.01)

(58) Field of Classification Search
CPC ................................ G06F 19/00; H04N 7/147
USPC ...... 345/173, 207, 633; 347/129; 348/14.08, 348/14.16, 14.03, 14.07; 351/206; 375/240.12; 382/293; 434/236; 463/32;
(Continued)

(56) References Cited

U.S. PATENT DOCUMENTS 6,466,250 B1 * 10/2002 Hein ...................... H04N 7/144
348/14.08
7,881,493 B1 2/2011 Edwards et al.
(Continued)

FOREIGN PATENT DOCUMENTS

JP 11-224152 8/1999
JP 2012-178135 9/2012

OTHER PUBLICATIONS

Extended European Search Report dated Jul. 27, 2016 issued in corresponding European Application No. 16151202.5.

*Primary Examiner* — Gerald Gauthier
(74) *Attorney, Agent, or Firm* — Harness, Dickey & Pierce, P.L.C.

(57) ABSTRACT

A communication terminal for communicating with a counterpart communication terminal includes a receiver that receives image data including an eye image of a user operating the counterpart communication terminal from the counterpart communication terminal, the eye image of the user being captured at the counterpart communication terminal while the user is viewing a predetermined position on a counterpart display and circuitry that specifies a sightline position indicating a sightline position of the user operating the counterpart communication terminal based on the received image data every time the image data is received by the receiver, determines a frequency of changes in the specified sightline position for a predetermined time period, and displays information indicating the frequency of changes in the specified sightline position on a display.

10 Claims, 14 Drawing Sheets

(51) Int. Cl.
*A61B 5/00* (2006.01)
*A61B 5/16* (2006.01)
*A61B 3/00* (2006.01)
*G06F 3/01* (2006.01)
*G06K 9/00* (2006.01)
*H04N 7/15* (2006.01)

(58) Field of Classification Search
USPC ....... 715/802, 863; 600/28, 300, 559; 607/2, 607/259; 705/2, 3, 51
See application file for complete search history.

(56) References Cited

U.S. PATENT DOCUMENTS

| | | | |
|---|---|---|---|
| 2002/0131498 A1* | 9/2002 | Sun | G06T 7/2026 375/240.12 |
| 2002/0165466 A1* | 11/2002 | Givens | A61B 5/121 600/559 |
| 2004/0101178 A1 | 5/2004 | Fedorovskaya et al. | |
| 2005/0110860 A1* | 5/2005 | Shiraishi | G02B 26/123 347/129 |
| 2006/0173708 A1* | 8/2006 | Vining | A61B 5/0002 705/2 |
| 2006/0271112 A1* | 11/2006 | Martinson | A61B 5/0031 607/2 |
| 2007/0066916 A1 | 3/2007 | Lemos | |
| 2009/0012419 A1 | 1/2009 | McKee | |
| 2010/0185990 A1* | 7/2010 | Ha | G06F 3/01 715/863 |
| 2011/0106557 A1* | 5/2011 | Gazula | G06Q 10/10 705/3 |
| 2011/0218674 A1* | 9/2011 | Stuart | G06F 19/321 700/259 |
| 2012/0029303 A1* | 2/2012 | Shaya | A61B 5/0022 600/300 |
| 2012/0232929 A1* | 9/2012 | Experton | G06Q 50/22 705/3 |
| 2012/0264514 A1* | 10/2012 | Lee | A63F 13/5255 463/32 |
| 2012/0278100 A1* | 11/2012 | Macoviak | G06F 19/327 705/3 |
| 2013/0033677 A1* | 2/2013 | MacDougall | A61B 3/113 351/206 |
| 2013/0102836 A1* | 4/2013 | Millman | A61M 21/02 600/28 |
| 2014/0192033 A1* | 7/2014 | Hsu | H04N 13/0409 345/207 |
| 2014/0207686 A1* | 7/2014 | Experton | G06F 19/3418 705/51 |
| 2014/0282235 A1* | 9/2014 | Minagawa | G06F 3/013 715/802 |
| 2014/0364761 A1 | 12/2014 | Benson et al. | |
| 2015/0050628 A1* | 2/2015 | Mori | A61B 5/167 434/236 |
| 2015/0085250 A1* | 3/2015 | Larsen | G06K 9/00604 351/206 |
| 2015/0123997 A1* | 5/2015 | Hayasaka | G02B 27/017 345/633 |
| 2015/0278989 A1* | 10/2015 | Lee | G06F 3/013 382/293 |
| 2015/0294079 A1* | 10/2015 | Bergougnan | G06F 19/3456 705/2 |
| 2015/0338914 A1* | 11/2015 | Andrysco | G06F 3/041 345/173 |
| 2016/0065896 A1* | 3/2016 | Chow | H04N 7/147 348/14.03 |
| 2016/0078680 A1* | 3/2016 | Reif | G06T 7/0044 345/633 |
| 2016/0210432 A1* | 7/2016 | Mizuhara | G06F 19/3418 |
| 2016/0234461 A1* | 8/2016 | Mizuhara | H04L 65/4023 |
| 2016/0252958 A1* | 9/2016 | Mizuhara | G06F 19/3418 348/14.07 |
| 2016/0261826 A1* | 9/2016 | Mizuhara | A61B 3/0025 |

* cited by examiner

FIG. 3

MEDICAL CHECKUP DATA

| NAME | SEX | AGE |
|---|---|---|
| TARO RICOH | MALE | 36 |

| CHECKED ITEMS | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| ERYTHROCYTE | 481 | 472 | 491 | 456 |
| NEUTRAL FAT | 172 | 178 | 173 | 167 |

| PAST MEDICAL HISTORY | ANSWERS |
|---|---|
| HIGH-BLOOD PRESSURE | YES |
| STROKE | NO |
| CANCER | NO |
| DIABETES | YES |
| ARRHYTHMIA | NO |
| BRONCHIAL ASTHMA | NO |

| LIFESTYLE HABITS | ANSWERS |
|---|---|
| EXERCISE HABIT | ONCE A WEEK |
| SMOKING | MORE THAN 10 PIECES A WEEK |
| DRINKING | 1 LITER A WEEK |
| SLEEPING TIME | 6 HOURS (AVE) |
| EAT FRIED FOODS | YES |
| CONSTIPATION | NO |
| FEEL STRESSED | NO |

FIG. 7

| USER ID | NAME | SEX | AGE |
|---------|------|-----|-----|
| 123456 | TARO RICOH | MALE | 36 |
| 123457 | HANAKO PENTA | FEMALE | 35 |
| ⋮ | ⋮ | ⋮ | ⋮ |

FIG. 8A

| USER ID | CHECKED ITEMS | 2014/05/01 | 2013/05/01 | 2012/05/01 | 2011/05/01 |
|---|---|---|---|---|---|
| 12345 | HEIGHT | 170.5 | 170.4 | 170.6 | 170.8 |
| | WEIGHT | 70.0 | 69.1 | 66.1 | 65.3 |
| | BMI | 24.2 | 23.8 | 22.8 | 22.4 |
| | BLOOD PRESSURE | 130 | 111 | 126 | 132 |
| | URIC ACID | 6.4 | 6.5 | 6.8 | 6.1 |
| | ERYTHROCYTE | 481 | 472 | 491 | 456 |
| | NEUTRAL FAT | 172 | 178 | 173 | 167 |

FIG. 8B

| USER ID | PAST MEDICAL HISTORY | ANSWERS |
|---|---|---|
| 12345 | HIGH-BLOOD PRESSURE | YES |
| | STROKE | NO |
| | CANCER | NO |
| | DIABETES | YES |
| | ARRHYTHMIA | NO |
| | BRONCHIAL ASTHMA | NO |

FIG. 8C

| USER ID | LIFESTYLE HABITS | ANSWERS |
|---|---|---|
| 12345 | EXERCISE HABIT | ONCE A WEEK |
| | SMOKING | MORE THAN 10 PIECES A WEEK |
| | DRINKING | 1 LITTER A WEEK |
| | SLEEPING TIME | 6 HOURS (AVE) |
| | EAT FRIED FOODS | YES |
| | CONSTIPATION | NO |
| | FEEL STRESSED | NO |

| PUPIL-CORNEAL REFLEX | DISPLAY POSITIONS |
|---|---|
| (1, −1) | DISPLAY AREA s1 (UPPER LEFT) |
| (−1, −1) | DISPLAY AREA s2 (UPPER RIGHT) |
| (1, 1) | DISPLAY AREA s3 (LOWER LEFT) |
| (−1, 1) | DISPLAY AREAs4 (LOWER RIGHT) |

TERMINAL, SYSTEM, DISPLAY METHOD, AND RECORDING MEDIUM STORING A DISPLAY PROGRAM

CROSS-REFERENCE TO RELATED APPLICATIONS

This patent application is based on and claims priority pursuant to 35 U.S.C. §119(a) to Japanese Patent Application No. 2015-039781, filed on Mar. 2, 2015 in the Japan Patent Office, the entire disclosures of which are hereby incorporated by reference herein.

BACKGROUND

Technical Field

The present invention relates to a terminal, a system, a display method, and a non-transitory recording medium storing a display program.

Background Art

Recently, videoconference systems for allowing a user to communicate with a counterpart at a remotely-located site via the Internet have been widely used. Since the videoconference systems allow the user to have conversation while watching a face of the counterpart, the user feels as he or she were having a face-to-face conversation with the counterpart locally.

It has become difficult to allocate industrial physicians to all offices from a viewpoint of labor cost. To cope with this issue, some industrial physicians use the videoconference systems to examine a patient at a remotely-located site.

SUMMARY

An example embodiment of the present invention provides a novel communication terminal for communicating with a counterpart communication terminal that includes a receiver that receives image data including an eye image of a user operating the counterpart communication terminal from the counterpart communication terminal, the eye image of the user being captured at the counterpart communication terminal while the user is viewing a predetermined position on a counterpart display and circuitry that specifies a sightline position indicating a sightline position of the user operating the counterpart communication terminal based on the received image data every time the image data is received by the receiver, determines a frequency of changes in the specified sightline position for a predetermined time period, and displays information indicating the frequency of changes in the specified sightline position on a display.

Further embodiments of the present invention provide a remote communication system, a display method, and a non-transitory recording medium storing a display program.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 3 is a diagram illustrating an employee-side screen as an embodiment of the present invention;

FIG. 7 is a conceptual diagram illustrating a user management table as an embodiment of the present invention;

FIG. 8A is a diagram illustrating a checkup result management table; FIG. 8B is a diagram illustrating a past medical history management table;

FIG. 8C is a diagram illustrating a lifestyle habits management table;

Figure 1:
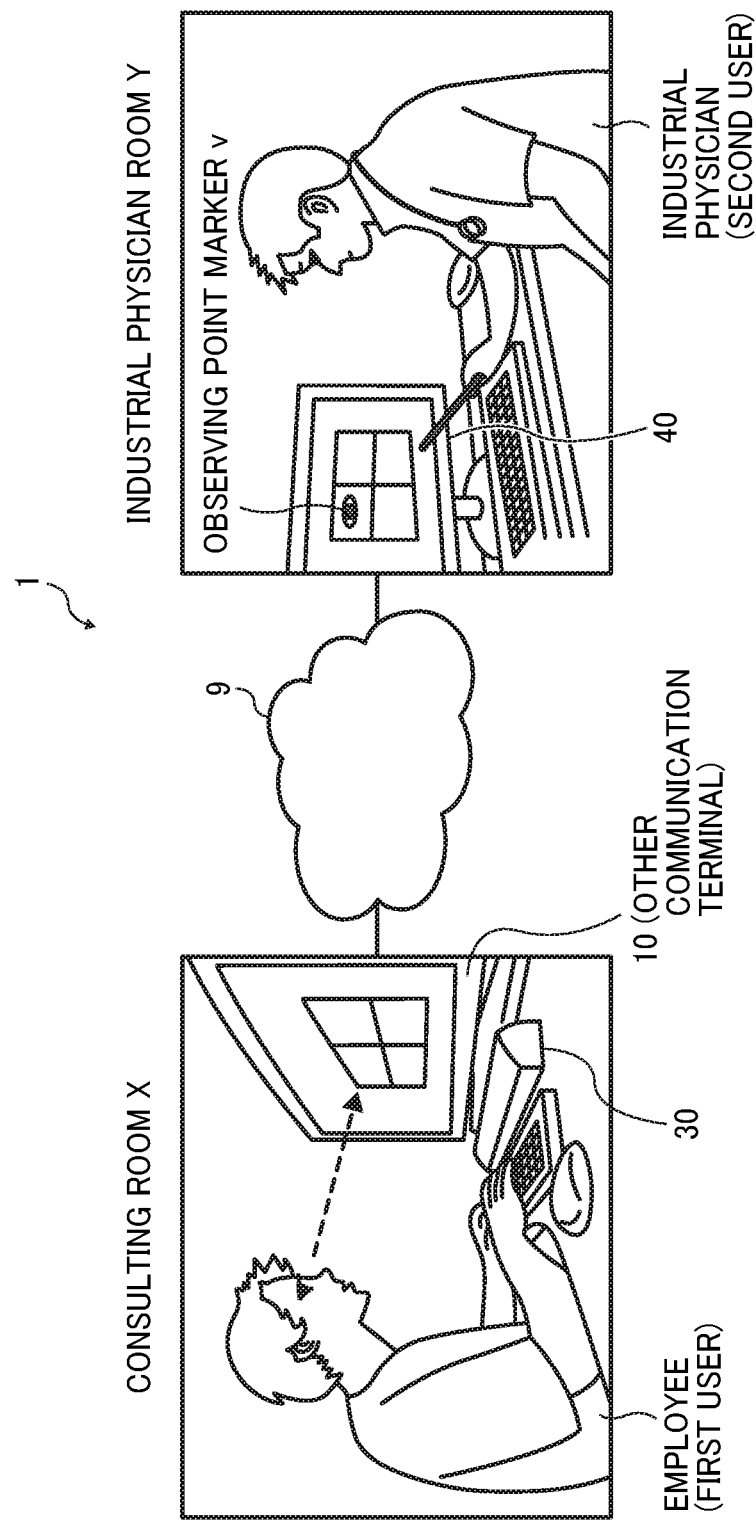
FIG. 1 is a schematic diagram illustrating a configuration of a consultation system as an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Referring to FIGS. 1 to 4, an embodiment of the present invention is described. FIG. 1 is a schematic diagram illustrating a configuration of a consultation system 1 according to the embodiment.

As shown in FIG. 1, the consultation system 1 in this embodiment includes an employee-side communication terminal 10, an employee-side sightline detection device 30, and an industrial-physician-side communication terminal 40. The communication terminal 10 and the sightline detection device 30 are located at a consultation room X where an employee visits for consultation with an industrial physician. The sightline detection device 30 is connected to the communication terminal 10 via a cable for transferring image data including at least an image of an eye of the employee. The communication terminal 40 is located at an industrial physician's room Y where the industrial physician works.

In this embodiment, general-purpose personal computers (PCs) are used for the communication terminals 10 and 40, and they are connected with each other communicably via a communication network 9 such as the Internet and a local area network (LAN).

It should be noted that any one of the communication terminals 10 and 40 may be implemented by a smartphone or a tablet device. Furthermore, at least the communication terminal 10 may be a terminal with a build-in sightline detection device 30, such that the communication terminal 10 may be dedicated to the remote consultation. In this disclosure, the communication terminal 10 may be referred to as a first communication terminal, or a counterpart communication terminal from a viewpoint of the communication terminal 40. The communication terminal 40 may be referred to as a second communication terminal.

For example, in FIG. 1, the consultation system 1 is used by the employee as an example of the first user, and the industrial physician as an example of the second user. The other example combinations of the first user and the second user include a corporate manager as the first user and the industrial physician as the second user, or the employee or the corporate manager as the first user and any other physician, a nurse, or a pharmacist as the second user. The other example combinations of the first user and the second user further include a teacher or an instructor as the first user and a student of any age or a guardian of the student as the second user. Furthermore, the other example combinations of the first user and the second user include a subordinate as the first user and a boss as the second user.

In FIG. 1, the sightline detection device 30 transfers image data acquired by capturing at least the employee's eye part to the communication terminal 10, and the communication terminal 10 transfers the image data to the communication terminal 40. Subsequently, the communication terminal 40 displays an observing point marker v based on the employee's sightline direction based on the image data. In this case, an eyeball-shaped marker is displayed as an example of the observing point marker v. As a result, even in case of having a remote consultation with the employee, the industrial physician can perceive, from the unstable sightline, that the employee has some concerns or seems to be depressed, just like the face-to-face consultation.

It should be noted that the observing point marker v indicating the employee's sightline direction is not displayed on the communication terminal 10. This is because the industrial physician cannot determine whether or not the employee is in a depression etc. precisely if the employee recognizes his/her own observing point marker v. In addition, the observing point marker v is an example of observing point information. Other examples of the observing point information include not displaying the marker but modifying color of texts or width of frames etc. displayed as the medical checkup data (described later).

Figure 2:
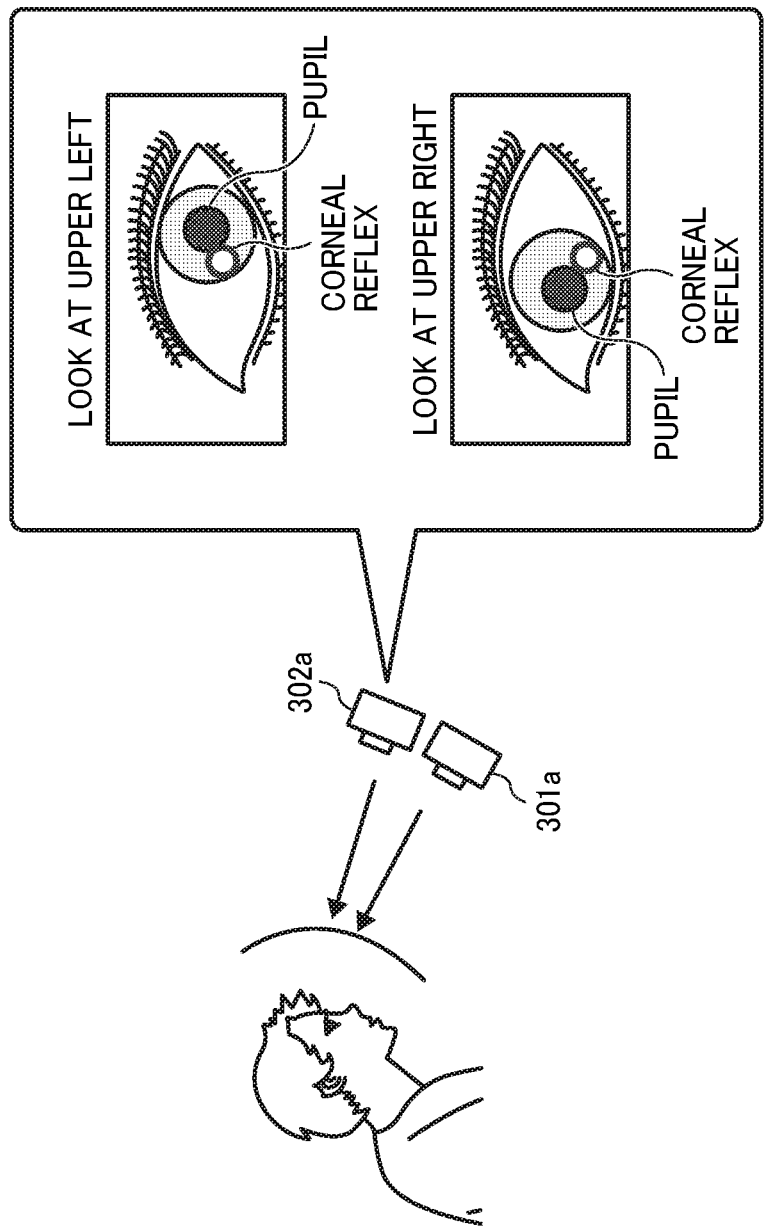
FIG. 2 is a schematic diagram illustrating a sightline detection method as an embodiment of the present invention.

Next, an outline of a sightline detection method is described below. FIG. 2 is a schematic diagram illustrating operation of detecting a sightline of the employee in this embodiment. The sightline detection method detects movements of the user's eyeballs to determine directions at which the user is looking. To start detecting movements of the user's eyeballs, firstly, a static part (reference point) and a movable part (moving point) of the user's eyes are detected at the detection device. After detecting the reference point and the moving point, the detection device detects the sightline of the user based on a position of the moving point in accordance with the reference point. There are various sightline detection methods, each of which differs in how the reference point and the moving point are each chosen. Among them, as a typical method, a corneal reflex sightline detection method in which a corneal reflex position is regarded as the reference point and a pupil position is regarded as the moving point to analyze their positional relationship is described below.

In general, the detection device for performing the sightline detection method has an infrared light emitting diode (LED) lighting device 301a, which illuminates the user's face, and determines a position of reflected light of the emitted light on the cornea (the corneal reflex) as the reference point. The detection device further has an infrared camera 302a, which detects the user's sightline based on the position of the pupil with reference to the position of the corneal reflex. For example, as shown in FIG. 2, if the pupil of the left eye is located at upper left compared to the position of the corneal reflex, it is detected that the user is looking at upper left. By contrast, if the pupil of the left eye is located at upper right compared to the position of the corneal reflex, it is detected that the user is looking at upper right. The detected sightline data is expressed as coordinate data.

Figure 4:
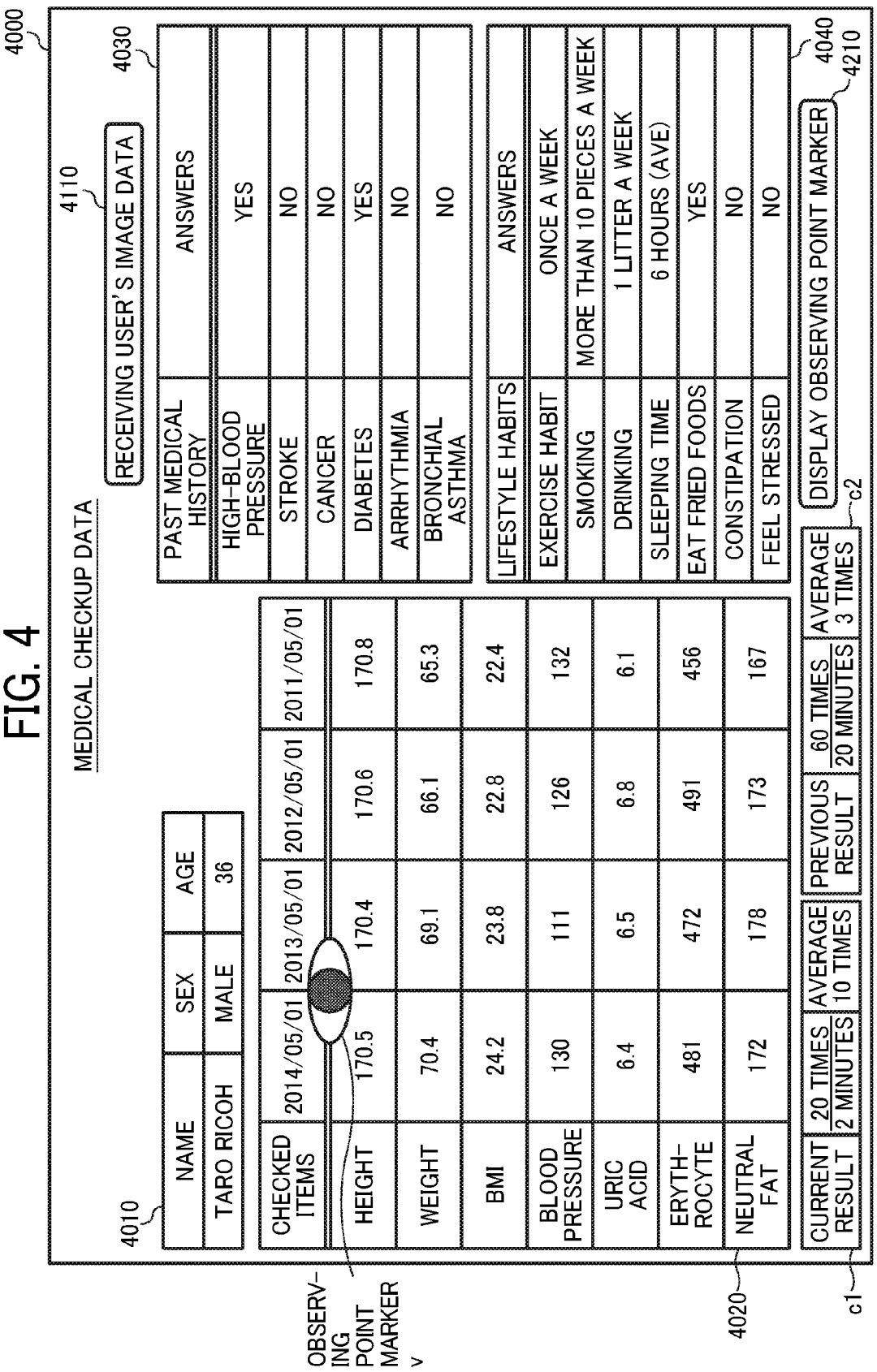
FIG. 4 is a diagram illustrating an industrial-physician-side screen as an embodiment of the present invention.

In this embodiment, the sightline detection method described above is applied to detect the first user's sightline during remote consultation, which is performed by the terminal 10 at the employee side in cooperation with the terminal 40 at the industrial physician side. As a result, in this embodiment, a screen shown in FIG. 3 is displayed on the communication terminal 10 on the employee side, and a screen shown in FIG. 4 is displayed on the communication terminal 40 on the industrial physician side.

Other examples of the sightline detection methods are an iris detection method using LMedS and an active appearance model (AAM) method etc. In the corneal reflex method, the iris detection method, and the AAM method, the sightline is detected based on image data indicating an image of a user. In the corneal reflex method, the coordinate data is output as the sightline data. By contrast, in the iris detection method and the AAM method, specific parameters are output as the sightline data. More specifically, in the iris detection method, an iris part of the user's eye is detected based on the image in which the user is captured, an ellipse is fit into the detected iris, and the sightline is detected based on three parameters, slope of the fit ellipse, major axis of the fit ellipse, and minor axis of the fit ellipse. In the AAM method, a face model is generated based on face images captured when the user faces into various directions, and the sightline is detected by storing (or learning) parameters of amount of characteristics acquired by associating the face models with the sightline directions.

FIG. 3 is a diagram illustrating an employee-side screen in this embodiment. FIG. 4 is a diagram illustrating an industrial-physician-side screen in this embodiment. As shown in FIG. 3, the communication terminal 10 displays a medical checkup data screen 1000 on a display 217 (described later). On the medical checkup data screen 1000, an employee's personal information display area 1010, a checkup result display area 1020, a medical history display area 1030, and a lifestyle habit display area 1040 are displayed. On the personal information display area 1010, the user's personal data such as employee name etc. is displayed. The medical checkup management data such as checkup results of the user's medical checkup etc. is displayed on the checkup result display area 1020, the medical history display area 1030, and the lifestyle habit display area 1040. That is, the user personal data and the medical checkup management data, which may be collectively referred to as the medical checkup data, is displayed as the content of the medical checkup data screen 1000. In this embodiment, the remote consultation is used for medical use. However, the purpose of the remote consultation is not limited to that. That is, it is possible to use the remote consultation for business use. As a result, the medical checkup data in this embodiment is an example of the user related data that indicates content related to the user. Other examples of the user related data are a performance result in an example case of a manager as the second user and a staff as the first user, a grade report or an examination sheet in an example case of a teacher as the second user and a student as the first user, an evidential photo or a questioning sheet in an example case of a detective as the second user and a suspect as the first user, and a fortune-telling result or an image of a palm in an example case of a fortune-teller as the second user and a customer as the first user.

By contrast, the communication terminal 40 displays a medical checkup data screen 4000 on a display 217 (described later). On the medical checkup data screen 4000, just like the screen of FIG. 3, a user's personal information display area 4010, a checkup result display area 4020, a medical history display area 4030, and a lifestyle habit display area 4040 are displayed. The user's personal information display area 4010, the checkup result display area 4020, the medical history display area 4030, and the lifestyle habit display area 4040 respectively display the same content as the corresponding user's personal information display area 1010, checkup result display area 1020, medical history display area 1030, and lifestyle habit display area 1040. The medical checkup data screen 4000 additionally displays an observing point marker v, a reception status display area 4110, and an observing point marker display button 4210. On the reception status display area 4110, a message indicating that the communication terminal 40 is receiving image data from the communication counterpart (i.e., the employee) is displayed. In this case, the message "receiving user's image data" is displayed as an example of the message. The observing point marker display button 4210 is a key pressed by the industrial physician to display the observing point marker v on the display 217 at the communication terminal 40. That is, the observing point marker display button 4210 accepts a command to display the observing point marker v from the industrial physician. It should be noted that the displayed position of the observing point marker v on the medical checkup data screen 4000 changes to reflect the employee's sightline direction that is currently detected.

Furthermore, on the medical checkup data screen 4000, change-related information $c_1$ related to a changed status of the display area including the current sightline position is displayed at lower left, and change-related information $c_2$ related to a changed status of the display area including the past (e.g., previous) sightline position is displayed at lower center. In FIG. 4, as examples of the change-related information $c_1$, in the remote consultation session this time, the current number of changed times is 20, two minutes elapsed after starting determining whether or not the display area is changed, and the average number of changed times is 10. In addition, as examples of the change-related information $c_2$, the previous number of changed times is 60, it took 20 minutes from starting determining whether or not the display area is changed to finishing the remote consultation, and the average number of changed times is 3.

Figure 5:
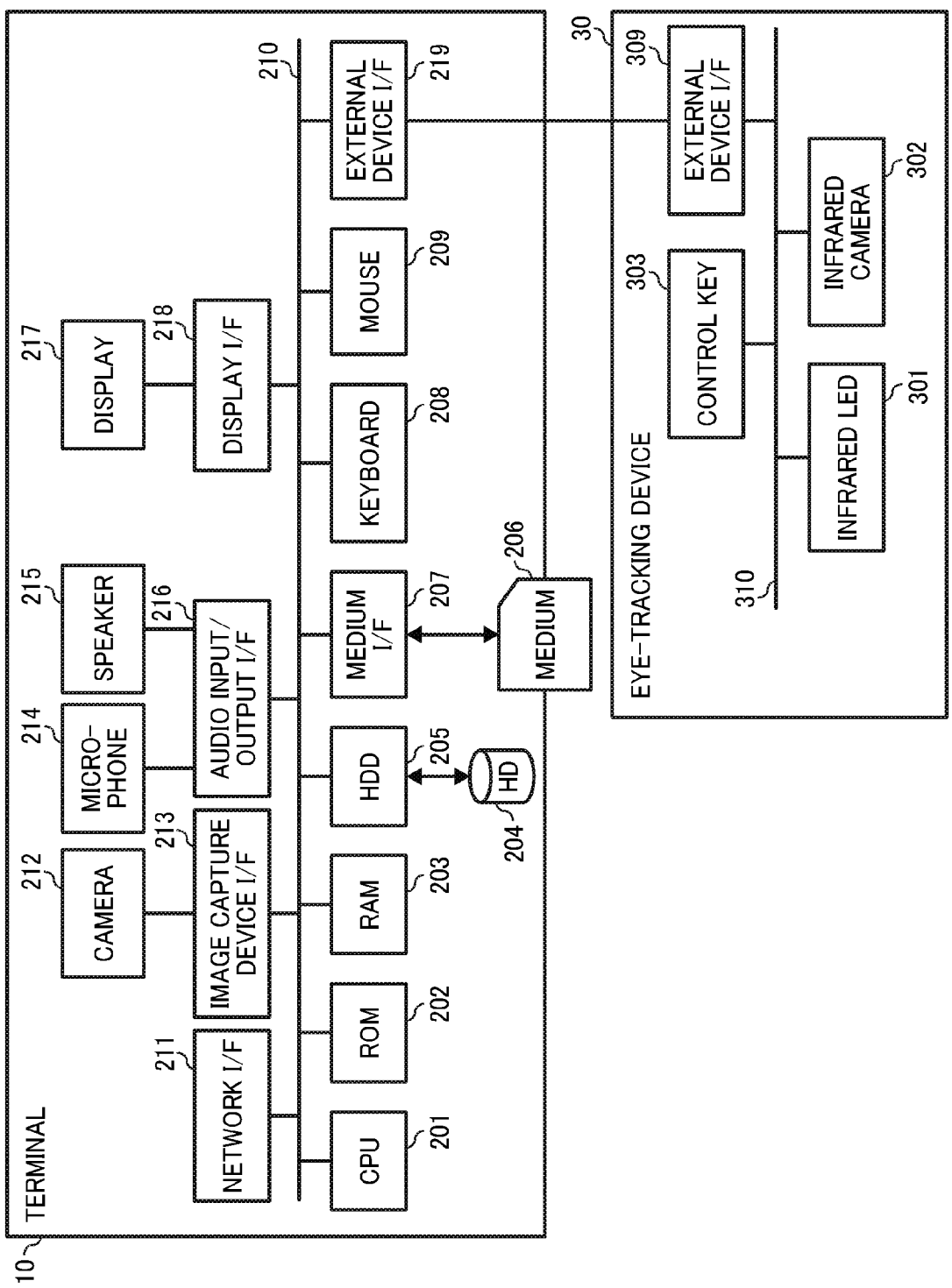
FIG. 5 is a diagram illustrating a hardware configuration of a communication terminal and a sightline detection device of the consultation system of FIG. 1 as the embodiment of the present invention.

Next, a hardware configuration of the communication terminals 10 and 40 and the sightline detection device 30 is described below with reference to FIG. 5. FIG. 5 is a diagram illustrating a hardware configuration of the communication terminal 10 and the sightline detection device 30 in this embodiment. Here, the communication terminal 40 has the same configuration as that of the communication terminal 10. Therefore, description of the communication terminal 40 is omitted, and the hardware configuration of the communication terminal 10 and the sightline detection device 30 is described below.

As shown in FIG. 5, the communication terminal 10 includes a central processing unit (CPU) 201, a read only memory (ROM) 202, a random access memory (RAM) 203, a hard disk (HD) 204, a hard disk drive (HDD) 205, a medium interface (I/F) 207, a keyboard 208, and a mouse 209.

Among those components, the CPU 201 controls entire operation of the communication terminal 10. The ROM 202 stores programs such as IPL etc. used for executing the CPU 201. The RAM 203 is used as a work area for the CPU 201. The HD 204 stores various data such as programs. The HDD 205 controls reading various data from the HD 204 and writing various data in the HD 204 under control of the CPU 201. The medium I/F 207 controls reading data from a recording medium such as a flash memory etc. and writing data in the recording medium 206. The keyboard 208 is an input device including multiple keys for inputting text, values, and various commands. The mouse 209 is an input device used for selecting or executing various commands, selecting a target to be processed, and moving a cursor etc.

In addition, the communication terminal 10 includes a network I/F 211, a camera 212, an image capture device I/F 213, a microphone 214, a speaker 215, an audio input/output I/F 216, a display 217, a display I/F 218, and an external device I/F 219.

Among those components, the network I/F 211 is an interface for transferring data via the communication network 9, such as a network interface card. The camera 212 captures a target object under control of the CPU 201 and outputs image data of the captured image. The image capture device I/F 213 is a circuit for controlling driving the camera 212. The microphone 214 is a built-in microphone for inputting audio such as audio of user's voice. The speaker 215 is a built-in speaker for outputting audio such as audio of the counterpart user's voice. The audio input/output I/F 216 is a circuit for processing input of an audio signal from the microphone 214 and output an audio signal to the speaker 215 under control of the CPU 201. The display 217 displays various information such as a cursor, a menu, a window, a text, a marker, and an image etc. The display I/F 218 outputs video (a still image and/or a movie) to the display 217 under control of the CPU 201. The external device I/F 219 is an interface for transferring data via a Universal Serial Bus (USB) cable etc.

Furthermore, the communication terminal 10 includes a bus line 210 such as an address bus and a data bus etc. for electrically connecting the components such as the CPU 201 described above with each other as shown in FIG. 5.

The programs described above may be stored as installable or executable files in a computer-readable recording medium such as the recording medium 206 described above for distribution. Alternatively, the programs described above may be stored not in the HD 204 but in the ROM 202. Other examples of the above-described recording medium include, but not limited to, a Compact Disc Recordable (CD-R), a Digital Versatile Disc (DVD), and a Blu-ray disc.

As shown in FIG. 5, the sightline detection device 30 includes an infrared LED lighting device 301, an infrared camera 302, a control key 303, an external device I/F 309, and a bus line 310.

Among those components, the infrared LED lighting device 301 is a lighting device including a diode that emits infrared light. The infrared camera 302 senses infrared. The external device I/F 309 is an interface for transferring data via a USB cable etc. The bus line 310 is a bus such as an address bus and a data bus etc. for electrically connecting the components such as the infrared LED lighting device 301 etc. described above with each other as shown in FIG. 5.

Figure 6:
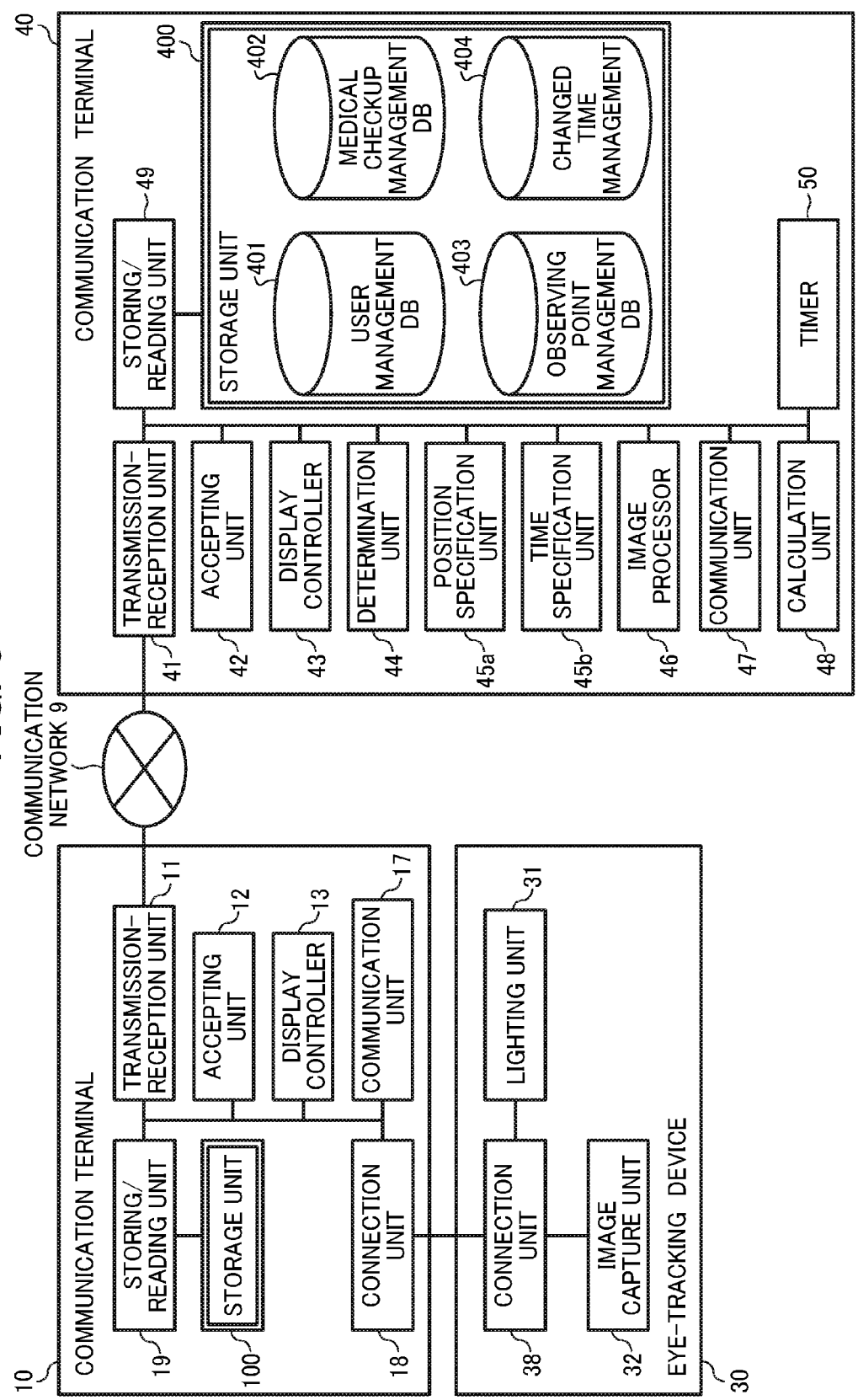
FIG. 6 is a diagram illustrating a functional configuration of the consultation system of FIG. 1.

Next, a functional configuration of the consultation system 1 in this embodiment is described below with reference to FIGS. 5 and 6. FIG. 6 is a diagram illustrating a functional configuration of the consultation system 1 in this embodiment.

As shown in FIG. 6, the communication terminal 10 includes a transmission-reception unit 11, an accepting unit 12, a display controller 13, a generator 14, a communication unit 17, a connection unit 18, and a storing/reading unit 19. Those components described above are functions or units implemented by operating some of the hardware components shown in FIG. 5 under control of the CPU 201 in accordance with programs expanded in the RAM 203 from the HD 204. In addition, the communication terminal 10 includes a storage unit 100 that may be implemented by the ROM 202, the RAM 203, and/or the HD 204 shown in FIG. 5.

The transmission-reception unit 11 in the communication terminal 10 is mainly implemented by processes performed by the network I/F 210 and the CPU 201 shown in FIG. 5. Mainly, the transmission-reception unit 11 transfers various data to the communication terminal 40 or receives various data from the communication terminal 40 via the communication network 9. For example, every time the infrared camera 302 captures an image of the employee at a predetermined interval, the transmission-reception unit 11 transmits sightline data indicating an employee's sightline direction.

The accepting unit 12 is mainly implemented by processes performed by the keyboard 208, the mouse 209, and the CPU 201 and accepts various selection, designation, or commands etc. by user operation.

The display controller 13 is mainly implemented by processes performed by the display I/F 218 and the CPU 201 and controls displaying various images and text on the display 217.

The generator generates sightline data based on image data including an image of the employee's eye acquired by an image capture unit 32 (described later). For example, in case of using the corneal reflex method described above is used, the sightline data is expressed as coordinate data.

The communication unit 17 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 40 to carry out communication between the communication terminals 10 and 40.

The connection unit 18, which is mainly implemented by processes performed by the external device I/F 209 and the CPU 201, detects a connection to an external device, and communicates with the external device that is connected.

The storing/reading unit 19 stores various data in the storage unit 100 and reads various data from the storage unit 100.

As shown in FIG. 6, the sightline detection device 30 includes a lighting unit 31, an image capture unit 32, and a connection unit 38. Those components described above are functions or units implemented by operating some of the hardware components in the sightline detection unit 30 shown in FIG. 5.

The lighting unit 31 is implemented by operations of the infrared LED lighting device 301 and illuminates the user face by emitting infrared light.

The image capture unit 32 is implemented by operations of the infrared camera 302 as an example of the image capture unit and captures reflected light of the infrared emitted by the lighting unit 31 to generate image data.

The connection unit 38, which is mainly implemented by processes performed by the external device I/F 309, detects a connection to an external device and communicates with the external device that is connected.

As shown in FIG. 6, the communication terminal 40 includes a transmission-reception unit 41, an accepting unit 42, a display controller 43, a determination unit 44, a position specification unit 45*a*, a time specification unit 45*b*, an image processor 46, a communication unit 47, a calculation unit 48, and a storing/reading unit 49. Those components described above are functions or units implemented by operating some of the hardware components shown in FIG. 5 under control of the CPU 201 in accordance with programs expanded in the RAM 203 from the HD 204. In addition, the communication terminal 40 includes a storage unit 400 that may be implemented by the ROM 202, the RAM 203, and/or the HD 204 shown in FIG. 5. The storage unit 400 stores therein a user management database (DB) 401, a medical checkup management DB 402, an observing point position management DB 403, and a changed time management DB 404. The user management DB 401 consists of a user management table shown in FIG. 7. The medical checkup management DB 402 consists of a checkup result management table, a medical history management table, and a lifestyle habit management table shown in FIG. 8. The observing point position management DB 403 consists of an observing point position management table shown in FIG. 9A. The changed time management DB 404 consists of a changed time management table shown in FIG. 10.

It should be noted that the user management table stores various data to be used as the contents of user personal data. The checkup result management table, the medical history management table, and the lifestyle habit management table together store various data to be used as the contents of the medical checkup management data. That is, in FIGS. 3 and 4, the user management table has contents to be displayed in the user personal information display area 1010 (4010), the checkup result management table has contents to be displayed in the checkup result display area 1020 (4020), the medical history management table has contents to be displayed in the medical history display area 1030 (4030), and the lifestyle habit management table has contents to be displayed in the lifestyle habit display area 1040 (4040).

FIG. 7 is a conceptual diagram illustrating a user management table in this embodiment. The user management table, which is used to manage user personal information, stores, for each user, a user ID for identifying the user, a user name, a user sex, and a user age associated with one another. It should be noted that the user ID is an example of user identification information for uniquely identifying a user. Examples of the user identification information include an employee number, a student number, and a social security number, which may be managed using the computerized personal data system.

FIG. 8A is a conceptual diagram illustrating the checkup result management table. The checkup result management table stores a plurality of checkup items and past checkup dates for each check item in association with the user ID. Examples of the checked items include height, weight, Body Mass Index (BMI), blood pressure, uric acid, erythrocyte, and neutral fat.

FIG. 8B is a conceptual diagram illustrating the medical history management table. The medical history checkup table stores a plurality of past medical history items and user answers to questions regarding the past medical history items, in association with the user ID. Examples of the past medical history items include high-blood pressure, stroke, cancer, diabetes, arrhythmia, and bronchial asthma. If the answer is "yes", that indicates that the user has been diagnosed as having that disease, and if the answer is "no", that indicates that the user has not been diagnosed as having that disease.

FIG. 8C is a conceptual diagram illustrating the lifestyle habits management table. The lifestyle habit management table stores a plurality of lifestyle habit items and user's answers to questions of lifestyle habits in association with the user ID. Examples of the lifestyle habit items include exercise habit, smoking, drinking, sleeping time, eating many fried foods, constipation, and feeling stressed. If the answer is "yes", that indicates that the user practices the lifestyle habit item, and if the answer is "no", that indicates that the user does not practice the lifestyle habit item.

Figures 9A, 9B:
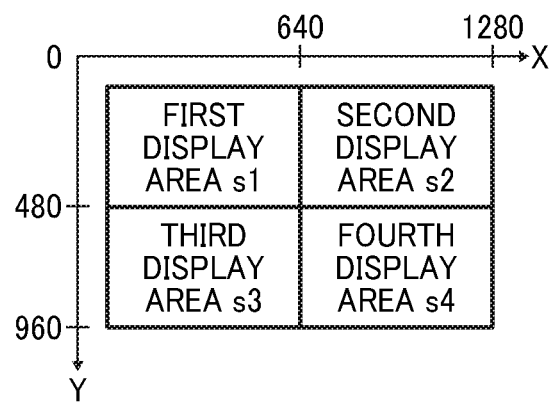
FIG. 9A is a diagram illustrating a sightline position management table.
FIG. 9B is a diagram for explaining a display area.

FIG. 9A is a conceptual diagram illustrating a sightline position management table. In this case, FIG. 9A illustrates a table used when the corneal reflex method is applied. The sightline position management table stores coordinate data indicating a position of the pupil against a position of the corneal reflex of a user eye, in association with display area information indicating a display area that includes a position of the user observing point on the display 217 of the communication terminals 10 and 40. It is also possible to indicate the coordinate data more circumstantially and associate the coordinate data with not the display area including the observing point position but the observing point position. In this case, "the display area" is comprehended in a concept of "the display position".

FIG. 9B is a conceptual diagram illustrating a display area. In FIG. 9B, the respective displays 217 of the communication terminals 10 and 40 have a size of 1280 pixels horizontally by 960 pixels vertically. The upper left area corresponds to a display area s1, the upper right area corresponds to a display area s2, the lower left area corresponds to a display area s3, and the lower right area corresponds to a display area s4. For example, if the coordinate data of the user's pupil is (1, −1), the observing point position is located within the display area s1. As a result, the observing point marker v is displayed within the display area s1 as shown in FIG. 4.

In case of using the iris detection method or the AAM method, parameters are managed associated with the display area information instead of the coordinate data.

Figure 10:
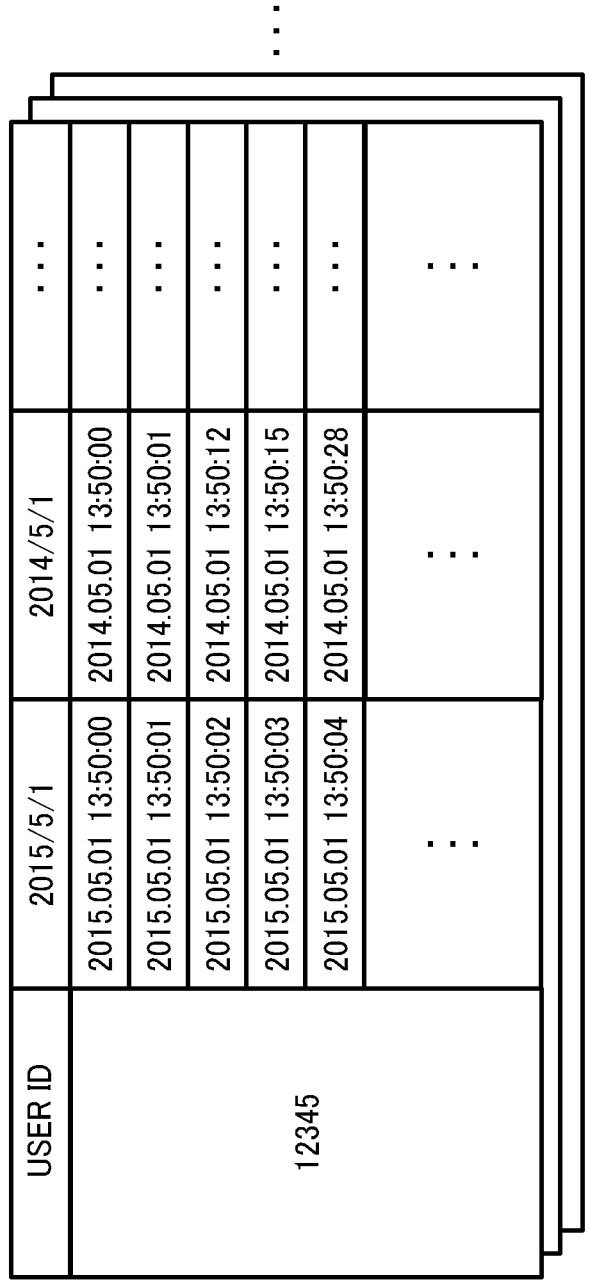
FIG. 10 is a conceptual diagram illustrating a changed time management table as an embodiment of the present invention.

FIG. 10 is a conceptual diagram illustrating a changed time management table in this embodiment. In the changed time management table, changed time information in the current remote consultation and the previous remote consultation is managed associated with the user ID. The changed time information indicates data and time when the employee's observing point position is changed from a predetermined display area to another display area. In the changed time information management table, the content of the record is added every time the display area including the employee's observing point position specified by the position specification unit 45a is changed. For example, if the consultation is carried out on May 1, 2015, in the first record from the top, date and time when the display area including the observing point position is specified for the first time (13:50:00, May 1, 2015) is managed. Subsequently, if the display area is changed, in the second record from the top, the changed time information indicating time when the display area is changed (13:50:01, May 1, 2015) is managed. The changed time information in the previous remote consultation is managed as changed history in the previous remote consultation. In FIG. 10, the changed time information on the day when the previous remote consultation is carried out (May 1, 2014) is managed as the changed history in the previous remote consultation. Since it is possible that the changed time information indicates time, it is possible that the changed time information does not indicate date.

Next, the functional configuration of the communication terminal 40 is described below with reference to FIGS. 5 and 6, according to the embodiment of the present invention.

The transmission-reception unit 41 in the communication terminal 40 is mainly implemented by processes performed by the network I/F 210 and the CPU 201 shown in FIG. 5. Mainly, the transmission-reception unit 41 transfers various data to the communication terminal 10 or receives various data from the communication terminal 10 via the communication network 9.

The accepting unit 42 is mainly implemented by processes performed by the keyboard 208, the mouse 209, and the CPU 201 and accepts various selection, designation, or commands etc. by user operation.

The display controller 43 is mainly implemented by processes performed by the display I/F 218 and the CPU 201 and controls displaying various images and text on the display 217.

The determination unit 44 is mainly implemented by processes performed by the CPU 201 and determines whether or not the image data is received from the communication terminal 10. In addition, the determination unit 44 determines whether or not the display area including the employee's observing point position specified by the position specification unit 45a is changed.

The position specification unit 45a is mainly implemented by processes performed by the CPU 201 and generates the coordinate data indicating the display area including the employee's observing point position by specifying the display area including the employee's observing point position on the display 217 of the communication terminal 40 based on the image data received by the transmission-reception unit 41 every time the transmission-reception unit 41 receives the image data.

The time specification unit 45b is mainly implemented by processes performed by the CPU 201 and includes a timing function. When the determination unit 45 determines that the display area including the employee's observing point position is changed, the time specification unit 45b specifies date and time when the display area including the employee's observing point position is changed. In addition, if the display area including the employee's observing point position is specified for the first time, the time specification unit 45b specifies time when the display area is specified for the first time since the observing point position is not always changed in that case.

The image processor 46 is mainly implemented by processes performed by the CPU 201 and superimposes the observing point marker v on the medical checkup data.

The communication unit 47 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 10 to carry out communication between the communication terminals 10 and 40.

The calculation unit 48 is mainly implemented by processes performed by the CPU 201 and calculates average number of changed times indicating the number of changed times per a predetermined period of time based on changed time information managed by the changed time management table in FIG. 10.

The storing/reading unit 49 stores various data in the storage unit 400 or reads various data from the storage unit 400.

The adjustment unity 51 adjusts the employee's sightline position specified by the specification unit 45 based on user calibration data managed by the user management table in FIG. 7A. For example, the adjustment unit 51 performs adjustment so that the employee's sightline position is moved from the first area (e.g., the hidden area h12) into the second area (e.g., the display area s1).

Figure 11:
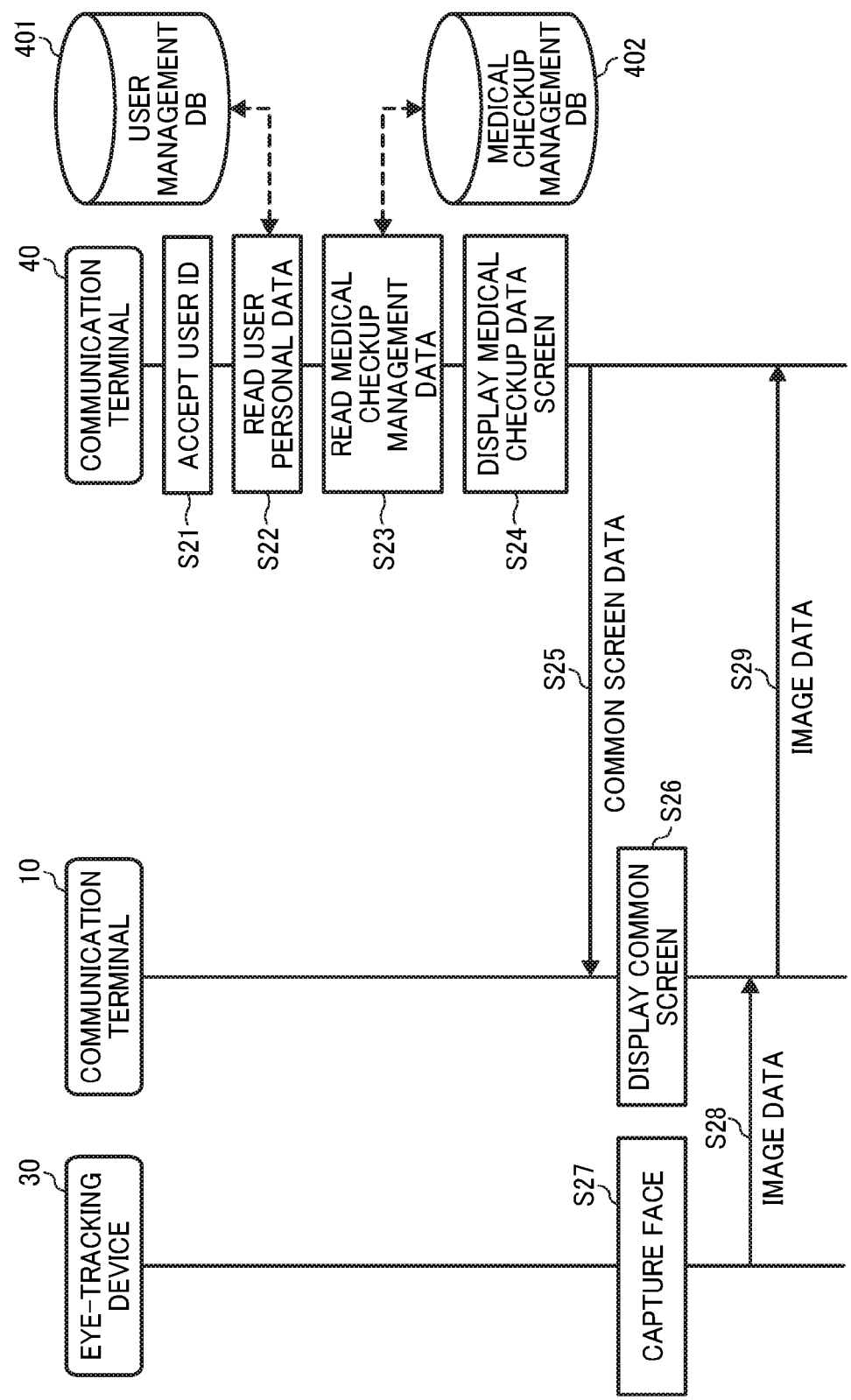
FIG. 11 is a sequence diagram illustrating operation of conducting a remote consultation, according to an embodiment of the present invention.
Figure 12:
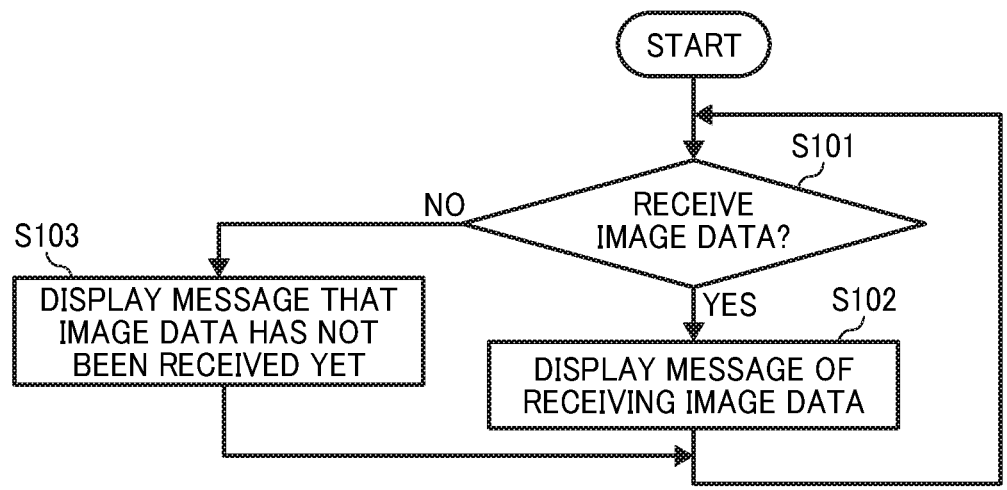
FIG. 12 is a flowchart illustrating operation of displaying a message on the industrial-physician-side screen, according to an embodiment of the present invention.

Next, processes and operations in this embodiment are described below with reference to FIGS. 11 to 14. FIG. 11 is a sequence diagram illustrating operation of carrying out a remote consultation. FIG. 12 is a flowchart illustrating operation of displaying a message on the industrial-physician-side screen.

First, just like the videoconference session, the employee and the industrial physician start the remote consultation using the communication terminals 10 and 40. At this point, the face of the user and at least a part of the room where the user resides at a counterpart site are displayed on the display 217 at a site where the user communicating with the counterpart user resides. As the industrial physician switches the current screen into an input screen and inputs the employee's user ID during the consultation, the accepting unit 42 receives input of the user ID in S21. The user ID is used when various data is searched through each of the table that the user ID is managed, stored in each of the table that the user ID is managed, and read from each of the table that the user ID is managed. Next, using the user ID accepted by the accepting unit 42 as a retrieval key, the storing/reading unit 49 searches through the user management table in the storage unit 400 (shown in FIG. 7) to read the user personal data indicating the corresponding user name, user sex, and user age for the user with the input user ID in S22. Furthermore, using the user ID accepted by the accepting unit 42 as the retrieval key, the storing/reading unit 49 searches through the medical checkup management table in the storage unit 400 (shown in FIG. 8) to read the medical checkup management data related to the corresponding user checkup items, user past medical history, and user lifestyle habits in S23. Subsequently, in the communication terminal 40, the display controller 43 displays the medical checkup data screen that consists of the user personal data and the medical checkup management data shown in FIG. 4 on the display 217 of the communication terminal 40 in S24. At this point, the observing point marker v and the message in the reception status display area 4110 have not been displayed yet.

Next, the transmission-reception unit 41 transfers shared screen data the same images as the display areas 4010, 4020, 4030, and 4040 to share the screen with the communication terminal 10 in S25. As a result, the transmission-reception unit 11 in the communication terminal 10 receives the shared screen data. Subsequently, in the communication terminal 10, the display controller 13 displays the medical checkup data screen shown in FIG. 3 on the display 217 of the communication terminal 10 in S26.

In addition, in the consultation room X, the lighting unit 31 in the sightline detection device 30 emits infrared light to the employee face, and the image capture unit 32 receives the reflected light to acquire the image data regarding the image including the employee eye in S27. The emission and reception operation are performed at a predetermined interval (e.g., every 0.5 seconds). Subsequently, the sightline detection device 30 transfers the image data from the connection unit 38 to the connection unit 18 in the communication terminal 10 in S28.

Next, the transmission-reception unit 11 in the communication terminal 10 transfers the image data to the communication terminal 40 via the communication network 9 in S29 As a result, the transmission-reception unit 41 in the communication terminal 40 receives the image data. The transmission/reception process of the image data described above is performed sequentially each time the sightline detection device 30 transfers the image data to the communication terminal 10 in S28.

Next, as shown in FIG. 12, in the communication terminal 40, the determination unit 44 determines whether or not the image data is received from the communication terminal 10 in S101. If the determination unit 44 determines that the sightline data is received (YES in S101), as shown in FIG. 4, the display controller 43 displays a receiving message indicating that the image data is being received in the reception status display area 4110 on the medical checkup data screen 4000 in S102. For example, as shown in FIG. 4, a message "receiving user's sightline data" is displayed as the receiving message. By contrast, if the determination unit 44 determines that the sightline data is not received from the communication terminal 10 (NO in S101), the display controller 43 displays a not-received message indicating that the sightline data has not been received yet in the reception status display area 4110 on the medical checkup data screen 4000 in S103. For example, a message "user's sightline data has not been received yet" is displayed as the not-received message. It should be noted that it is possible not to display a message if the image data has not been received.

Figure 13:
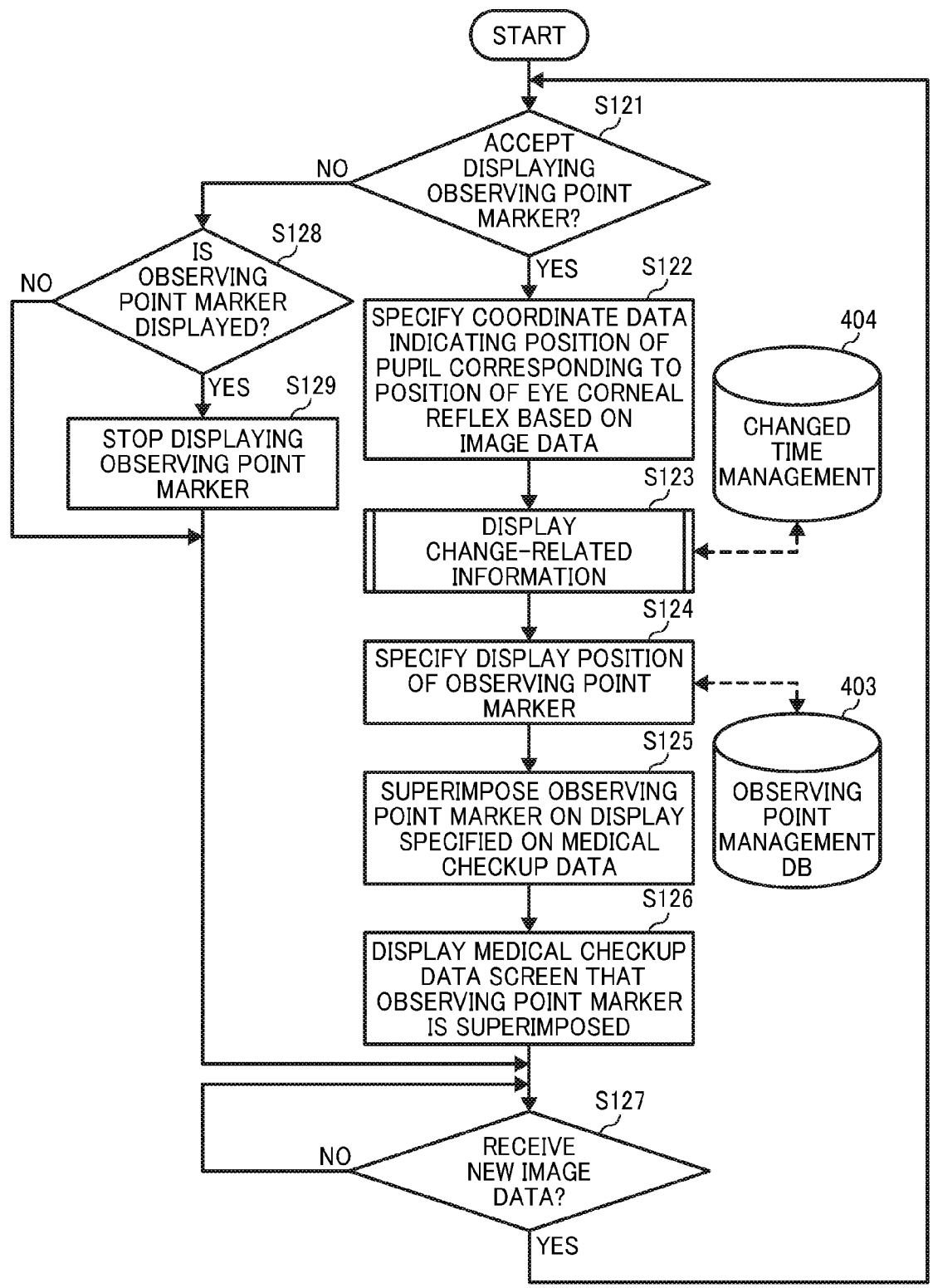
FIG. 13 is a flowchart illustrating operation of displaying an observing point marker on the industrial-physician-side screen, according to an embodiment of the present invention.
Figure 14:
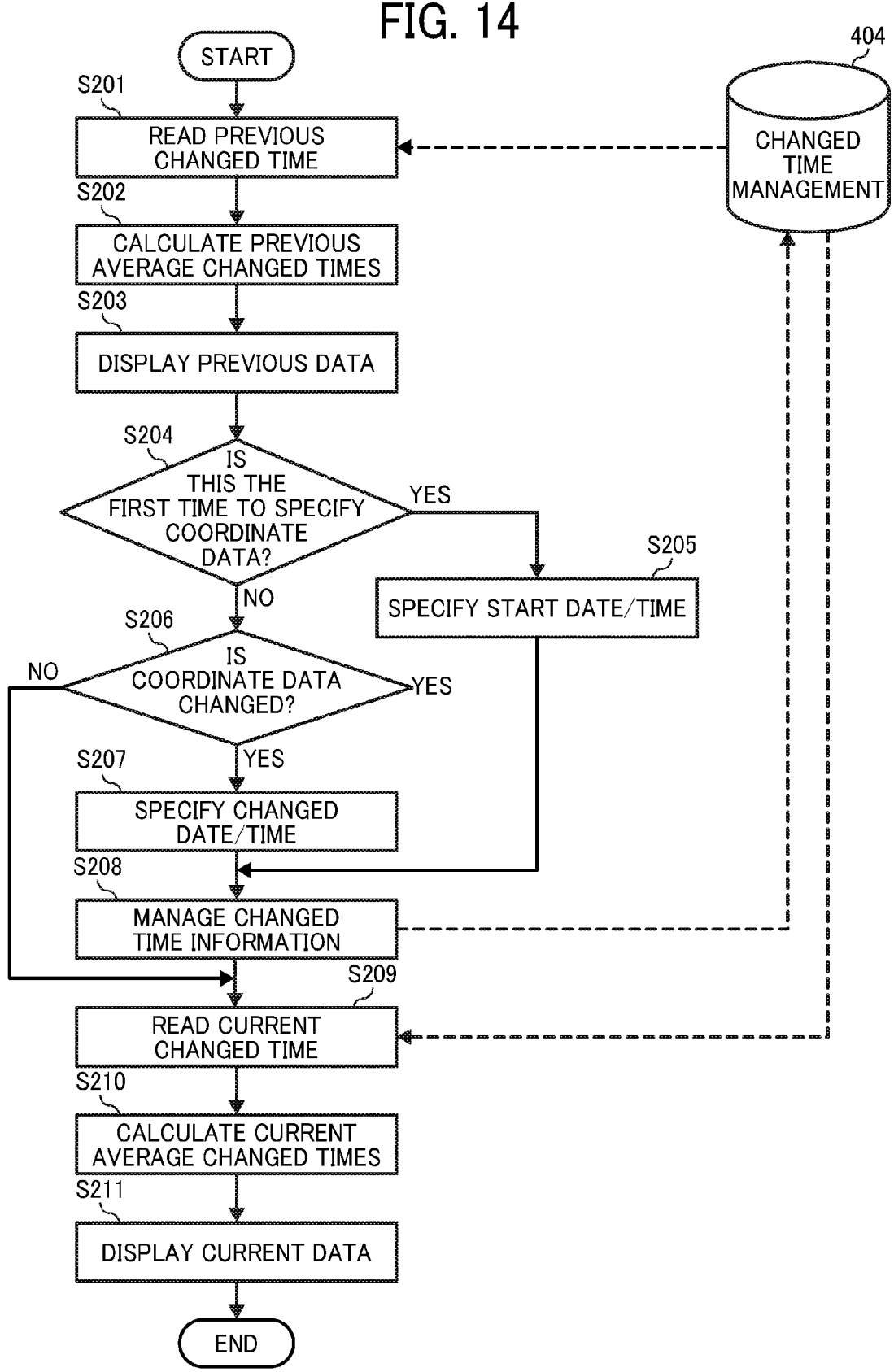
FIG. 14 is a flowchart illustrating operation of displaying change related information related to change of a display area including an employee's observing point position.

Next, processes and operations of displaying the observing point marker v on the industrial-physician-side screen in this embodiment are described below with reference to FIGS. 13 and 14. FIG. 13 is a flowchart illustrating operation of displaying the observing point marker on the industrial-physician-side screen.

Furthermore, as shown in FIG. 15, in the communication terminal 40, the determination unit 44 determines whether or not the accepting unit 42 accepts that the industrial physician requests to display the observing point marker v in S121. If the determination unit 44 determines that the request has been received (YES in S121), the position specification unit 45a specifies coordinate data indicating a position of pupil against a position of corneal reflex of the eye based on the image data in S122.

Next, as shown in the lower part of FIG. 4, the communication terminal 40 displays the change-related information c1 regarding the change of the display area including the current observing point position and the change-related information c2 regarding the change of the display area indicating the past (i.e., previous) observing point position in S123. Here, with reference to FIGS. 4 and 14, operation of displaying the change related information related to the change of the display area including the employee's observing point position is described below. FIG. 14 is a flowchart illustrating operation of displaying the change related information related to the change of the display area including the employee's observing point position.

First, using the user ID accepted in S21 as a retrieval key, the storing/reading unit 49 searches through the changed time management table in FIG. 10 to read the previous changed time information of the employee who currently carries out the consultation in S201. In this case, the previous changed time information is read among the past changed time information.

Next, in S202, the calculation unit 48 calculates the average changed times indicating the number of changed times per a predetermined period of time based on the changed time information read in S201. For example, the predetermined period of time is one minute. Assuming that the changed times in the previous remote consultation was 60 and the consultation time is 20 minutes, the number of average changed times becomes three. Subsequently, the display controller 43 displays the past (i.e., previous in this case) change-related information c2 in the lower center part on the medical checkup data screen 4000 of the communication terminal 40.

Next, after accepting the request on displaying the observing point marker v, the determination unit 44 determines whether or not the position specification unit 45a specifies the coordinate data for the first time in S204. If it is determined that the coordinate data is specified for the first time (YES in S204), the time specification unit 45b specifies the current date/time when the position specification unit 45a specifies as starting date/time to manage changed time information in the current remote consultation in S205.

By contrast, if it is determined that the coordinate data is not specified for the first time (NO in S204), the determination unit 44 further determines whether or not the coordinate data (the display area including the observing point position) is changed in S206. If it is determined that the coordinate data is changed (YES in S206), the time specification unit 45b specifies the current date/time when the position specification unit 45a specifies as the changed time when the coordinate data is changed in S207. Subsequently, in the field of the date of the current remote consultation in the changed time management table in FIG. 10, the storing/reading unit 49 stores the changed time information indicating the changed date/time from the top of the record downwardly to manage the changed time information in S208. If the starting date/time is specified in S205, the changed time information indicates the starting date/time.

Next, the storing/reading unit 49 reads the current changed time information of the employee who carries out the consultation currently from the changed time management table in FIG. 10 in S209.

Next, in S210, the calculation unit 48 calculates the average changed times indicating the number of changed times per a predetermined period of time based on the changed time information read in S209. Here, the predetermined period of time is the same as the case in S202. For example, assuming that the changed times in the previous remote consultation was 20 and two minutes elapses after specifying the starting date/time in S205, the number of average changed times becomes three. Subsequently, the display controller 43 displays the current change-related information c1 in the lower left part on the medical checkup data screen 4000 of the communication terminal 40 in S211. As a result, the operation in S123 ends.

In FIG. 13, by searching through the sightline position management table in FIG. 9A using the coordinate data specified in S122 as the retrieval key, the position specification unit 45a specifies a display position of the observing point marker v by reading corresponding display position information in S124.

Next, the image processor 46 superimposes the observing point marker v at the display position specified in S124 described above on the medical checkup data in S125. Subsequently, in the communication terminal 40, as shown in FIG. 4, the display controller 43 displays the medical checkup data screen 4000 on which the observing point marker v is imposed on the display 217 of the communication terminal 40 in S126.

After that, the determination unit 44 determines whether or not new image data is received in S127. Subsequently, in S126, if the determination unit 44 determines that the new image data is received (YES in S127), the process goes back to the step in S121. By contrast, in S127, if the determination unit 44 determines that the request has not been received yet (NO in S127), the determination unit 44 repeats the step in S127. For example, the repetition process is performed every one second.

By contrast, in S121, if the determination unit 44 determines that the request to display the observing point marker v has not been received yet (NO in S121), the determination unit 44 further determines whether or not the display controller 43 has already been displaying the observing point marker v in S128. If the determination unit 44 determines that the display controller 43 has already been displaying the observing point marker v (YES in S128), the display controller 43 stops displaying the observing point marker v in FIG. 4 in S129, and the process proceeds to S127. If the determination unit 44 determines that the display controller 43 is not displaying the observing point marker v (NO in S128), the process proceeds to S127. As shown in FIG. 4, if the observing point marker v is kept displaying on the medical checkup data screen 4000, the industrial physician might feel that it is difficult to recognize the medical checkup data screen 4000 in some cases. Therefore, it is possible to switch the observing point marker v from being displayed to not being displayed.

As described above, by displaying the observing point marker v on the display 217 of the communication terminal 40 on the industrial physician's side, the industrial physician can carry out the remote consultation considering the employee's sightline just like the face-to-face consultation. By using the communication terminal in this embodiment described above, it is possible to carry out the remote interview with quality similar to the face-to-face interview.

For example, as shown in FIG. 4, in case of displaying the observing point marker v at a position different from the employee's name even if the industrial physician confirms the employee's name through the communication the industrial physician can recognize that the employee is in some kind of abnormal condition such as depression.

Especially, if positions where the observing point marker v vary frequently under control of the display controller 43 based on the image data transferred from the communication terminal 10 sequentially, the industrial physician can further recognize that the employee is in abnormal condition more easily since the employee's sightline is unstable.

In addition, as shown in FIG. 4, since the changed status of the display area of the observing point marker v is indicated as the change-related information c1 using a specific numeric value, the industrial physician can recognize that the employee is in some kind of abnormal condition such as depression more easily.

In addition, as shown in FIG. 4, by referring to the change-related information c1 in the current remote consultation and the change-related information c2 of the same employee simultaneously, the industrial physician can determine the employee's health condition easily.

Numerous additional modifications and variations are possible in light of the above teachings. It is therefore to be understood that, within the scope of the appended claims, the disclosure of this patent specification may be practiced otherwise than as specifically described herein.

For example, while the above-described embodiment describes the case where an image of both eyes of the user is used to detect the user's sightline, at least one eye of the user may be captured as long as the user's sightline can be detected. For instance, if the user's dominant eye can be specified, the user's sightline may be detected using the image of the user's dominant eye.

As can be appreciated by those skilled in the computer arts, this invention may be implemented as convenient using a conventional general-purpose digital computer programmed according to the teachings of the present specification. Appropriate software coding can readily be prepared by skilled programmers based on the teachings of the present disclosure, as will be apparent to those skilled in the software arts. The present invention may also be implemented by the preparation of application-specific integrated circuits or by interconnecting an appropriate network of conventional component circuits, as will be readily apparent to those skilled in the relevant art.

Each of the functions of the described embodiments may be implemented by one or more processing circuits. A processing circuit includes a programmed processor. A processing circuit also includes devices such as an application specific integrated circuit (ASIC) and conventional circuit components arranged to perform the recited functions.

What is claimed is:

1. A first communication terminal for communicating with a counterpart communication terminal, the first communication terminal comprising:
   a receiver configured to receive image data including an eye image of a user operating the counterpart communication terminal from the counterpart communication terminal, the eye image of the user being captured at the counterpart communication terminal and indicating which of a plurality of positions on a counterpart display the user is viewing when the eye image is captured, the counterpart display being a display of the counterpart terminal; and
   circuitry configured to,
      display a first screen on a first display, the first display being a display of the first communication terminal,
      cause the counterpart terminal to display the first screen on the counterpart display by transferring shared screen data to the counterpart terminal,
      specify a sightline position indicating a sightline position of the user operating the counterpart communication terminal based on the received image data when the image data is received by the receiver,
      determine a frequency of changes in the specified sightline position for a first time period, and
      cause information indicating the frequency of changes in the specified sightline position to be displayed on the first and counterpart displays.

2. The first communication terminal according to claim 1, wherein the circuitry is configured to,
   determine whether or not the specified sightline position changes over the first time period to generate a determination result, and
   display a number of times that the specified sightline position changes as the frequency of changes in the specified sightline position, based on the determination result.

3. The first communication terminal according to claim 1, wherein the circuitry is configured to,
   counts the first time period from a time when the circuitry starts specifying the sightline of the user, and
   displays information indicating the first time period on the display in addition to the information indicating the frequency of changes in the specified sightline position.

4. The first communication terminal according to claim 3, wherein the circuitry is configured to,
   obtain change time information indicating a time when the sightline position changes if the circuitry determines that the specified sightline position changes,
   store the change time information when the circuitry that the specified sightline position has changed in a memory,
   calculate an average value of change times indicating the number of times that the specified sightline position changes per a unit of time based on the stored change time information, and
   display the calculated average value of change times on the display.

5. The first communication terminal according to claim 1, wherein the first time period is a time period that begins when the circuitry starts specifying the sightline of the user for communication currently performed by the user.

6. The first communication terminal according to claim 5, wherein the circuitry is configured to display information indicating the frequency of changes in the specified sightline position, respectively, for the first time period and a second time period, the second time period being a time period when the circuitry starts specifying the sightline position of the user for communication previously performed by the user prior to the communication currently performed by the user.

7. The first communication terminal according to claim 1, wherein the circuitry is configured to display sightline information indicating the sightline position of the user at the specified sightline position on the display.

8. A system, comprising the first communication terminal according to claim 1.

9. A display method, performed by a first communication terminal in communication with a counterpart communication terminal, the method comprising:
   receiving image data including an eye image of a user operating the counterpart communication terminal from the counterpart communication terminal, the eye image of the user being captured at the counterpart communication terminal and indicating which of a plurality of positions on a counterpart display the user is viewing when the eye image is captured, the counterpart display being a display of the counterpart terminal;

displaying a first screen on a first display, the first display being a display of the first communication terminal;

causing the counterpart terminal to display the first screen on the counterpart display by transferring shared screen data to the counterpart terminal;

specifying a sightline position indicating a sightline position of the user operating the counterpart communication terminal based on the received image data when the image data is received by the receiver;

determining a frequency of changes in the specified sightline position for a first time period; and causing information indicating the frequency of changes in the specified sightline position to be displayed on the first and counterpart displays.

10. A non-transitory computer-readable recording medium storing computer-readable instructions that, when executed by one or more processors, cause the one or more processors to perform operations including:

receiving image data including an eye image of a user operating a counterpart communication terminal from the counterpart communication terminal, the eye image of the user being captured at the counterpart communication terminal and indicating which of a plurality of positions on a counterpart display the user is viewing when the eye image is captured, the counterpart display being a display of the counterpart terminal;

displaying a first screen on a first display, the first display being a display of the first communication terminal;

causing the counterpart terminal to display the first screen on the counterpart display by transferring shared screen data to the counterpart terminal;

specifying a sightline position indicating a sightline position of the user operating the counterpart communication terminal based on the received image data when the image data is received by the receiver;

determining a frequency of changes in the specified sightline position for a first time period; and causing information indicating the frequency of changes in the specified sightline position to be displayed on the first and counterpart displays.

\* \* \* \* \*